United States Patent
Dyballa et al.

(10) Patent No.: US 9,765,023 B2
(45) Date of Patent: Sep. 19, 2017

(54) COMPLEXES OF DIPHENYL SELENOXIDES, USE THEREOF AND CATALYSIS METHODS

(71) Applicant: EVONIK DEGUSSA GMBH, Essen (DE)

(72) Inventors: Katrin Marie Dyballa, Recklinghausen (DE); Robert Franke, Marl (DE); Detlef Selent, Rostock (DE); Armin Börner, Rostock (DE); Claudia Weilbeer, Bernburg (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/371,675

(22) Filed: Dec. 7, 2016

(65) Prior Publication Data
US 2017/0158632 A1 Jun. 8, 2017

(30) Foreign Application Priority Data

Dec. 7, 2015 (EP) .................................... 15198150
Apr. 8, 2016 (DE) ........................ 10 2016 205 888

(51) Int. Cl.
 C07C 391/00 (2006.01)
 C07C 391/02 (2006.01)
 C07C 45/28 (2006.01)

(52) U.S. Cl.
 CPC ............ *C07C 391/02* (2013.01); *C07C 45/28* (2013.01)

(58) Field of Classification Search
None
See application file for complete search history.

(56) References Cited

U.S. PATENT DOCUMENTS 4,642,388 A * 2/1987 Young ..................... C07C 45/49
568/454
2015/0336865 A1 11/2015 Dyballa et al.
2015/0336885 A1 11/2015 Dyballa et al.
2015/0336995 A1 11/2015 Dyballa et al.
2016/0340304 A1 11/2016 Dyballa et al.

FOREIGN PATENT DOCUMENTS

EP 3095779 A1 11/2016
WO 2015/181018 A1 12/2015
WO 2016/139245 A1 9/2016

OTHER PUBLICATIONS

Izumi et al. Journal of Catalysis 132, 566-570 (1991).*
European Search Report issued Feb. 16, 2017 for EP 16 20 1660 (4 pages).
Weilbeer et al. Evaluation of Organoselenium Based Compounds as Co-Catalysts in Rhodium-Catalyzed Hydroformylation. ChemistrySelect, 1, 2016, 5421-5429.
Paetzold et al. Untersuchungen an Selen-Sauerstoff-Verbindungen, XXXVIII, Donator-Akzeptor-Komplexe von Diphenylselenoxid mit Metallchloriden. Zeitschrift Fur Anorganische Uno Allgemeine Chemie., 347, 1966, 294-303.
Ziegler et al. Extraktiv-photometrische Bestimmung von Rhodium unter Verwendung von Dipbenylselenoxid. Microchimica Acta, 1967, 782-787.
Klapötke et al. Synthesis and Structures of Bis(pentafluorophenyl) Selenoxide I Telluroxide, Zeitschrift fur Naturforschung, 2002, 145-150.
Potash et al. A General and Efficient Method to Convert Selenides into Selenones by Using HOF•CH $_3$CN. European Journal of Organic Chemistry, 2013, 25, 2013, 5574-5579.
Klapötke et al. New Aspects in the Chemistry of Aromatic and Fluoroaromatic Selenium and Tellurium Compounds: Similarities and Diversities. Phosphorus, Sulfur and Silicon and the Related Elements, 2001, 172:1, 119-128.
Khurana et al. Aqueous sodium hypochlorite mediated chemoselective oxidation of chalcogenides to monoxides and dioxides by microwave exposure. Can. J. Chem. 88, 2010, 906-909.

* cited by examiner

*Primary Examiner* — Sudhakar Katakam
*Assistant Examiner* — Ana Z Muresan
(74) *Attorney, Agent, or Firm* — Smith, Gambrell & Russell, LLP

(57) ABSTRACT

Novel complexes of diphenyl selenoxides and also use thereof and methods in which the complexes are used.

1 Claim, No Drawings

COMPLEXES OF DIPHENYL SELENOXIDES, USE THEREOF AND CATALYSIS METHODS

Novel complexes of diphenyl selenoxides and also use thereof and methods in which the complexes are used.

A synthetic route for the preparation of diphenyl selenides, as disclosed in the experimental section, is also described in the European patent application EP15168377.8. The resulting diphenyl selenides may subsequently be oxidized to diphenyl selenoxides.

In hydroformylation, monophosphites and biphosphites are generally used, which are often formed from biphenol units, The development of novel ligands is frequently limited by the available ligand building blocks. For instance, diphenyl selenoxides represent a highly interesting compound class which is suitable as a ligand in complexes or as ligand building blocks for the preparation of ligands.

The object of the invention was to provide a further wholly novel substance class of ligand building blocks and catalysts in order to broaden the field of available ligands for the respective specific complexes in catalysis. The object also consisted of providing or producing ligands for rhodium hydroformylation catalysts. The object therefore also consisted of providing novel ligand building blocks which serve as intermediates for preparing ligands. An additional object consisted of providing ligands or ligand building blocks for specific control of the catalysis.

The objects are achieved by diphenyl selenoxides which are aryl-bifunctionalized on the selenium. Furthermore, the objects are achieved by complexes comprising these diphenyl selenoxides. The diphenyl selenoxides according to the invention are selected from unsubstituted or substituted diphenyl selenoxides of the structure I, and also preferably of the structures Ia, Ib, Ib*, Ic and Id, and also of mixtures comprising at least two of the aforementioned structures.

The invention provides a complex comprising at least one diphenyl selenoxide having a general structure (I)

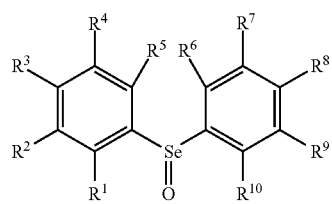
(I)

where $R^2$, $R^3$, $R^4$, $R^5$, $R^6$, $R^7$, $R^8$ and $R^9$ may be each independently selected from —H, —($C_1$-$C_{12}$)-alkyl, -halogen, where alkyl is linear, branched or cyclic, wherein the alkyl groups are each independently unsubstituted or optionally an aforementioned alkyl may be substituted by at least one —($C_3$-$C_{12}$)-cycloalkyl group, where $R^1$ and $R^{10}$ are each independently selected from —H, —($C_1$-$C_{12}$)-alkyl and/or -halogen, where alkyl is linear, branched or cyclic and at least one metal atom selected from Rh, Ru, Co, Ir. It may be preferable in accordance with the invention if all alkyl groups are unsubstituted.

Particularly preferred complexes comprise as at least one metal atom Rh, Ir, Ru, wherein Rh is particularly preferred.

The terms diphenyl selenoxide and olefin are used as generic terms in this application and therefore include in each case, in addition to the unsubstituted compounds, also the substituted compounds.

In one embodiment, the complex comprises at least one diphenyl selenide having a general structure (Ia)

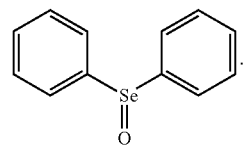
(Ia)

In one embodiment, the complex comprises at least one diphenyl selenide having a general structure (Ib)

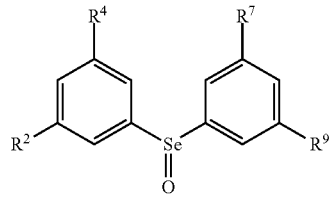
(Ib)

wherein in structure Ib, $R^2$, $R^4$, $R^7$ and $R^9$ are each independently selected from —($C_1$-$C_{12}$)-alkyl.

In one embodiment, the complex comprises at least one diphenyl seienide having a general structure (Ib*)

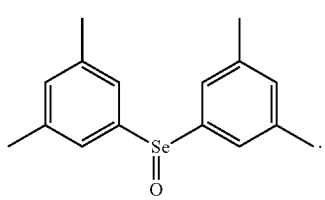
(Ib*)

In one embodiment, the complex comprises at least one diphenyl selenide having a general structure (Ic)

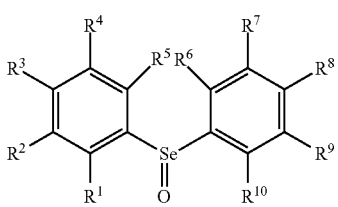
(Ic)

where $R^3$, $R^5$, $R^8$ and $R^8$ are in each case —H and $R^2$, $R^4$, $R^7$ and $R^9$ are each independently selected from —($C_1$-$C_{12}$)-alkyl, where alkyl is linear, branched or cyclic, and where $R^1$, $R^{10}$ are each independently selected from —H, —($C_1$-$C_{12}$)-alkyl and halogen, where alkyl is linear, branched or cyclic.

In one embodiment, the complex comprises at least one diphenyl selenide having a general structure (Id)

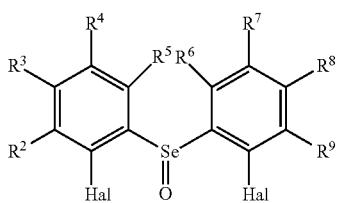

(Id)

where $R^2$, $R^3$, $R^4$, $R^5$, $R^6$, $R^7$, $R^9$, $R^9$ are each independently selected from —H, —$(C_1\text{-}C_{12})$-alkyl and -halogen.

In the context of the invention, the expression "—$(C_1$-$C_{12})$-alkyl" encompasses straight-chain and branched alkyl groups. Preferably, these groups are unsubstituted straight-chain or branched —$(C_1\text{-}C_8)$-alkyl groups and most preferably —$(C_1\text{-}C_6)$-alkyl groups. Examples of —$(C_1\text{-}C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propyibutyl, n-octyl, 2-ethylhexyl, 2-propylheptyl, nonyl, decyl.

Halogen (Hal) includes chlorine, bromine, fluorine and iodine, wherein particular preference is given to chlorine and fluorine.

The elucidations relating to the expression —$(C_1\text{-}C_{17})$-alkyl apply to all alkyl groups.

According to one embodiment variant, $R^2$, $R^3$, $R^4$, $R^5$, $R^6$, $R^7$, $R^8$ and $R^9$ may in each case correspond to an alkyl substituted by at least one —$(C_3\text{-}C_{12})$-cycloalkyl group, the —$(C_3\text{-}C_{12})$-cycloalkyl in the context of the present invention including mono-, bi- or tricyclic hydrocarbon residues having 3 to 12, particularly 5 to 12 carbon atoms. These include cyclopropyl, cyclobutyl, cyclopentyl, cyclohexyl, cycloheptyl, cyclooctyl, cycloclodecyl, cyclopentadecyl, norbornyl or adamantyl. One example of a substituted cycloalkyl would be menthyl.

Particularly preferred complexes comprise at least one rhodium atom and at least one diphenyl selenoxide of the structure Ia, Ib, Ib*, Ic and/or Id, wherein preferably in the structure Ic $R^1$ and $R^{10}$ are each independently selected from —H or —$(C_1\text{-}C_{12})$-alkyl, where alkyl is linear, branched or cyclic, and in the structure Ic $R^1$ and $R^{10}$ are preferably both identical and selected from —H or —$(C_1\text{-}C_6)$-alkyl, where alkyl is branched or cyclic.

Particularly preferred complexes comprise at least one ruthenium atom and at least one diphenyl selenoxide of the structure Ia, Ib, Ib*, Ic and/or Id, wherein preferably in the structure Ic $R^1$ and $R^{10}$ are each independently selected from —H or —$(C_1\text{-}C_{12})$-alkyl, where alkyl is linear, branched or cyclic, and in the structure Ic $R^1$ and $R^{10}$ are preferably both identical and selected from —H or —$(C_1\text{-}C_6)$-alkyl, where alkyl is branched or cyclic.

Particularly preferred complexes comprise at least one cobalt atom and at least one diphenyl selenoxide of the structure Ia, Ib, Ib*, Ic and/or Id, wherein preferably in the structure Ic $R^1$ and $R^{10}$ are each independently selected from —H or —$(C_1\text{-}C_{12})$-alkyl, where alkyl is linear, branched or cyclic, and in the structure Ic $R^1$ and $R^{10}$ are preferably both identical and selected from —H or —$(C_1\text{-}C_6)$-alkyl, where alkyl is branched or cyclic.

Particularly preferred complexes comprise at least one iridium atom and at least one diphenyl selenoxide of the structure Ia, Ib, Ib*, Ic and/or Id, wherein preferably in the structure Ic $R^1$ and $R^{10}$ are each independently selected from —H or —$(C_1\text{-}C_{12})$-alkyl, where alkyl is linear, branched or cyclic, and in the structure Ic $R^1$ and $R^{10}$ are preferably both identical and selected from —H or —$(C_1\text{-}C_6)$-alkyl, where alkyl is branched or cyclic.

With particular preference, $R^2$, $R^4$, $R^7$, $R^9$, in the structure I are each mutually independently selected from —H, —$(C_1\text{-}C_{12})$-alkyl and -halogen and $R^1$, $R^3$, $R^5$, $R^6$, $R^8$, $R^{10}$ are —H.

Diphenyl selenoxides of the structure I are particularly preferred where $R^1$ and $R^{10}$ and preferably both are —H or —$(C_1\text{-}C_{12})$-alkyl, where alkyl is linear, branched or cyclic, or $R^1$ is —H and $R^{10}$ is —$(C_1\text{-}C_{12})$-alkyl, where alkyl is linear, branched or cyclic. Alkyl is preferably selected from methyl, ethy, isopropyl, tert-butyl, isopentyl, 1,1-dimethylpropyl. $R^2$, $R^3$, $R^4$, $R^5$, $R^6$, $R^7$, $R^8$, $R^9$ are preferably —H.

Diphenyl selenoxides of the structure I are particularly preferred where $R^1$ is —H and $R^{10}$ is -halogen. $R^2$, $R^3$, $R^4$, $R^5$, $R^6$, $R^7$, $R^8$, $R^9$ are independently selected from —H, —$(C_1\text{-}C_{12})$-alkyl, where alkyl is linear, branched or cyclic.

Further preferred diphenyl selenoxides are where $R^2$, $R^4$, $R^7$ and $R^9$ are methyl, where $R^1$ and $R^{10}$ are both -halogen, —H or —$(C_1\text{-}C_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^2$, $R^4$, $R^5$, $R^6$, $R_7$ and $R^9$ are methyl, where $R^1$ and $R^{10}$ are both -halogen, —H or —$(C_1\text{-}C_6)$-alkyl, particularly methyl, ethyl, isopropyl, tert-butyl, isopentyl, 1,1-dimethylpropyl. $R^3$ and $R^8$ are preferably —H.

Further preferred diphenyl selenoxides are where $R^2$ and $R^9$ are isopropyl and $R^4$, $R^5$, $R^6$ and $R^7$ are methyl and where $R^1$ and $R^{10}$ are both -halogen, —H or —$(C_1\text{-}C_6)$-alkyl, particularly methyl, ethyl, isopropyl, tert-butyl, isopentyl, 1,1-dimethylpropyl. $R^3$ and $R^8$ are preferably —H.

Further preferred diphenyl selenoxides are where $R^2$ and $R^9$ are isopropyl and $R^5$ and $R^6$ are methyl, $R^4$ and $R^7$ are -halogen, in particular $R^4$ and $R^7$ are both —chlorine, where $R^1$ and $R^{10}$ are both -halogen, —H or —$(C_1\text{-}C_6)$-alkyl, particularly methyl, ethyl, isopropyl, tert-butyl, isopentyl, 1,1-dimethylpropyl. $R^3$ and $R^8$ are preferably —H.

Further preferred diphenyl selenoxides are where $R^2$ and $R^9$ are methyl and $R^4$ and $R^7$ are -halogen, in particular $R^4$ and $R^7$ are both —chlorine, where $R^1$ and $R^{10}$ are both -halogen, —H or —$(C_1\text{-}C_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^4$ and $R^7$ are methyl and $R^2$ and $R^9$ are -halogen, in particular $R^2$ and $R^9$ are both —bromine, where $R^1$ and $R^{10}$ are both -halogen, —H or —$(C_1\text{-}C_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^4$ and $R^7$ are tert-butyl and $R^2$ and $R^9$ are methyl, where $R^1$ and $R^{10}$ are both -halogen, —H or —$(C_1\text{-}C_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^2$, $R^4$, $R^7$ and $R^9$ are tert-butyl, where $R^1$ and $R^{10}$ are both -halogen, —H or —$(C_1$-$C_6)$-alkyl, particularly methyl, ethyl, isopropyl, tert-butyl, isopentyl, 1,1-dimethylpropyl, $R^3$, $R^5$, $R^6$, $R^8$ are preferably —H.

Further preferred diphenyl selenoxides are where $R^4$ and $R^7$ are ethyl and $R^2$ and $R^9$ are tert-butyl, where $R^1$ and a$^{10}$ are both -halogen, —H or —$(C_1$-$C_5)$-alkyl, particularly methyl, ethyl, isopropyl, tert-butyl, isopentyl, 1,1-dimethylpropyl. $R^3$, $N^5$, $R^4$, are preferably —H.

Further preferred diphenyl selenoxides are where $R^4$ and $R^7$ are ethyl and $R^2$ and $R^9$ are isopentyl, where $R^1$ and $R^{10}$ are both -halogen, —H or —$(C_1$-$O_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^2$, $R^4$, $R^7$ and $R^9$ are isopentyl, where $R^1$ and $R^{10}$ are both -halogen, —H or —$(C_1$-$C_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^4$ and $R^7$ are isopentyl and $R^2$ and $R^9$ are methyl, where $R^1$ and $R^{10}$are both -halogen, —H or —$(C_1$-$C_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^2$, $R^4$, $R^7$ and $R^9$ are -halogen, in particular $R^2$ and $R^9$ are both -chlorine and $R^4$ and $R^7$ are both -fluorine or $R^2$, $R^4$, $R^7$ and $R^9$ are each -fluorine, where $R^1$ and $R^{10}$ are both -halogen, —H or —$(C_1$—$C_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^2$, $R^4$, $R^7$and $R^9$ are 1,1-dimethylpropyl, where $R^1$ and $R^{10}$are both -halogen, —H or —$(C_1$-$C_6)$-alkyl, particularly methyl, ethyl, isopropyl, tert-butyl, isopentyl, 1,1-dimethylpropyl. $R^3$, $R^5$, $R^6$, $R^8$ are preferably —H.

Further preferred diphenyl selenoxides are where $R^2$, $R^4$, $R^7$ and $R^9$ are methyl, where $R^3$ and $R^8$ are both -halogen, —H or —$(C_1$-$C_6)$-alkyl, particularly methyl, ethyl, isopropyl, tert-butyl, isopentyl, 1,1-dimethylpropyl. $R^1$, $R^5$, $R^6$, $R^{10}$ are preferably —H.

With particular preference, $R^2$, $R^3$, $R^4$, $R^5$, $R^6$, $R^7$, $R^8$, $R^9$, $R^1$ and $R^{10}$ in diphenyl selenoxides of the structure I are each independently selected from —H and —$(C_1$-$C_{12})$-alkyl, in particular methyl, ethyl, propyl, isopropyl, n-butyl, isobutyl, sec-butyl, tert-butyl, n-pentyl, 2-pentyl, 2-methylbutyl-, 3-methylbutyl-, 1,2-dimethylpropyl-, 1,1-dimethylpropyl.

With particular preference, $R^2$, $R^3$, $R^4$, $R^5$, $R^6$, $R^7$, $R^8$, $R^9$, $R^1$ and $R^{10}$ diphenyl selenoxides of the structure I are each independently selected from —$(C_1$-$C_{12})$-alkyl, in particular methyl, ethyl, propyl, isopropyl, n-butyl, isobutyl, sec-butyl, tert-butyl, n-pentyl, 2-pentyl, 2-methylbutyl-, 3-methylbutyl-, 1,2-dimethylpropyl-, 1,1-dimethylpropyl.

With particular preference, $R^2$, $R^3$, $R^4$, $R^5$, $R^6$, $R^7$, $R^8$, $R^9$, $R^1$ and $R^{10}$ in diphenyl selenoxides of the structure I are each independently selected from —H and -halogen, selected from chlorine, bromine, fluorine, iodine.

With particular preference, $R^2$, $R^3$, $R^4$, $R^5$, $R^6$, $R^7$, $R^8$, $R^9$, $R^1$ and $R^{10}$ in diphenyl selenoxides of the structure I are -halogen, selected from chlorine, bromine, fluorine and iodine.

The diphenyl selenoxide of the structure I may be a substituted diphenyl selenoxide where $R^1$ to $R^{10}$ are independently selected from —H, —$(C_1$-$C_{12})$-alkyl and/or -halogen, preferably as defined above, wherein at least one of $R^1$ to $R^{10}$ is other than —H.

The diphenyl selenoxide of the structure I may be a substituted diphenyl selenoxide, where $R^2$, $R^3$, $R^4$, $R^7$, $R^8$ and $R^9$ may be each independently selected from —H, —$(C_1$-$C_{12})$-alkyl, -halogen, where alkyl is linear, branched or cyclic, wherein the alkyl groups are each independently unsubstituted or optionally an aforementioned alkyl may be substituted by at least one —$(C_3$-$C_{12})$-cycloalkyl group, where $R^1$, $R^5$, $R^6$ and $R^{10}$ are each independently selected from —H, —$(C_1$-$C_{12})$-alkyl and/or -halogen, where alkyl is linear, branched or cyclic and at least one metal atom selected from Rh, Ru, Co, Ir. It may be preferable in accordance with the invention if all alkyl groups are unsubstituted.

The diphenyl selenoxide of the structure I may be a substituted diphenyl selenoxide, where $R^2$, $R^3$, $R^4$, $R^7$, $R^8$ and $R^9$ may be each independently selected from —H, —$(C_1$-$C_{12})$-alkyl, -halogen, where alkyl is linear, branched or cyclic, wherein the alkyl groups are each independently unsubstituted or optionally an aforementioned alkyl may be substituted by at least one —$(C_3$-$C_{12})$-cycloalkyl group, where $R^1$, $R^5$, $R^6$ and $R^{10}$ are each independently selected from —H and/or -halogen, and at least one metal atom selected from Rh, Ru, Co, Ir. It may be preferable in accordance with the invention if all alkyl groups are unsubstituted.

The invention further relates to the use of a diphenyl selenoxide of the general structure

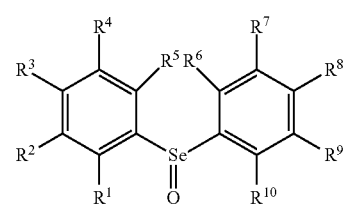

(I)

where $R^2$, $R^3$, $R^4$, $R^5$, $R^6$, $R^7$, $R^8$ and $R^9$ are each independently selected from —H, —$(C_1$-$C_{12})$-alkyl, -halogen, where alkyl is linear, branched or cyclic, wherein the alkyl groups are each independently unsubstituted or optionally an aforementioned alkyl may be substituted by at least one —$(C_3$-$C_{12})$-cycloalkyl group, where $R^1$ and $R^{10}$ are each independently selected from —H, —$(C_1$-$C_{12})$-alkyl and halogen, where alkyl is linear, branched or cyclic, a) as ligand in a complex comprising at least one metal atom or b) as intermediate for preparing ligands where $R^1$ and $R^{10}$) are -halogen. In this case, the structures of the diphenyl selerioxide, correspond to the above definitions.

Here, the selenium compound of the structure I can have the above mentioned substitution pattern and be an unsubstituted diphenyl selenide where $R^1$ to $R^{10}$ is —H or be a substituted diphenyl selenide with $R^1$ to $R^{10}$ as defined above, wherein at least one of $R^1$ to $R^{10}$ is other than —H or be an unsusbstituted diphenyl selenoxide where $R^1$ to $R^{10}$is —H or be a substituted diphenyl selenoxide with $R^1$ to $R^{18}$ as defined above, wherein at least one of $R^1$ to $R^{10}$ is other than —H, at least $R^1$ or $R^{10}$ is other than —H.

In accordance with particularly preferred embodiments, the invention relates to the use of a diphenyl selenoxide of the general structure I a) where $R^2$, $R^3$, $R^4$, $R^5$, $R^6$, $R^7$, $R^8$ and $R^9$ are each independently selected from —H, —$(C_1$-$C_{12})$-alkyl, -halogen, where alkyl is linear, branched or cyclic, where $R^1$, $R^{10}$ are —H and/or —$(C_1$-$C_{12})$-alkyl, where alkyl is linear, branched or cyclic, for the catalysis of a hydroformylation reaction, or b) where $R^2$, $R^3$, $R^4$, $R^8$, $R^6$, $R^7$, $R^8$ and $R^9$ are each independently selected from —H, —$(C_1$-$C_{12})$-alkyl, -halogen, where alkyl is linear, branched or cyclic, as intermediate for preparing ligands where $R^1$ and $R^{10}$ are -halogen.

The invention also relates to a method comprising the steps of (i) initially charging at least one olefin,
(ii) adding a complex comprising
at least one diphenyl selenoxide having a general structure I

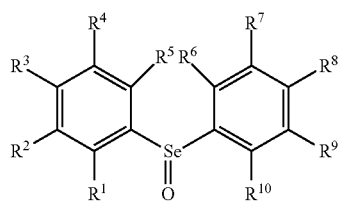

(I)

where $R^2$, $R^3$, $R^4$, $R^5$, $R^6$, $R^7$, $R^8$ and $R^9$ are each independently selected from —H, —$(C_1$-$C_{12})$-alkyl, -halogen, where alkyl is linear, branched or cyclic, wherein the alkyl groups are each independently unsubstituted or optionally an aforementioned alkyl can be substituted by at least one —$(C_3$-$C_{12})$-cycloalkyl group, where $R^1$ and $R^{10}$ are each independently —H, —$(C_1$-$C_{12})$-alkyl and/or -halogen, where alkyl is linear, branched or cyclic, wherein the alkyl groups are each independently unsubstituted or optionally an aforementioned alkyl can be substituted by at least one —$(C_3$-$C_{12})$-cycloalkyl group, and at least one metal atom selected from Rh, Ru, Co, Ir , particularly Rh, Ir, Ru, preferably Rh, or at least one diphenyl selenoxide of the general structure I, as described above, and a substance having a metal atom selected from Rh, Ru, Co, Ir, (iii) feeding in $H_2$ and CO,
(iv) heating the reaction mixture, wherein the olefin is converted to an aldehyde.

The method steps (i), (ii), (iii) and (iv) can alternatively be carried out in any sequence. In the method, a complex comprising a diphenyl selenoxide of the structure I, Ia, Ib, Ib*, Ie or Id can preferably be used or a corresponding diphenyl selenoxide of the structure I, Ia, Ib, Ib*, Ic or Id and a substance having an aforementioned metal atom can be used.

If necessary, a further liquid may be used as solvent.

In this case, preferably using the compounds according to the invention of the structures I, Ia, Ib, Ib*, Ie or Id in a hydroformylation according to the abovementioned use or abovementioned method, a yield of equal to or greater than 80%, in particular 85% and/or an n-regiosele,ctivity of greater than 20%, in particular equal to or greater than 25%, may be achieved, wherein in strucure I $R^1$ and $R^{10}$) are each independently selected from —H, —$(C_1$-$C_{12})$-alkyl and halogen, where alkyl is linear, branched or cyclic.

The invention is further illustrated in detail below by examples without the invention being limited to the working examples.

GENERAL METHODS

Solvents and Reagents All reactions with moisture- and/or oxygen-sensitive, substances were carried out in baked-out apparatuses under an argon atmosphere. Solvents for extraction and column chromatography were used at the following purities: dichloromethane (99.9%, Walter, Cat. No. BlE 073107033), ethyl acetate (99.5%, Walter, Cat. No. BlE 003917025) and n-hexane (95%, Walter (Baked, Cat. No. 8669), n-heptane (95%, Walter (Baker), Cat. No. 8662). Other solvents for extraction and column chromatography were of technical quality and were used without further purification unless otherwise stated. Dry solvents (abs.) were purified using a Pure Solv MD-7 System and stored under an argon atmosphere. Benzyl bromide was freshly distilled (17 mbar/82° C.) prior to use. Deuterated solvents were distilled from the drying agents specified:

dichloromethane-$d_2$ (phosphorus pentoxide), toluene-$d_8$ (1. KOH; 2. sodium). Chemicals used for the syntheses were supplied by Sigma Aldrich, Alfa Aesar, Acros Organics, Avantor Performance Materials B.V., Merck KGaA and ABCR GmbH & Co. KG. These were used without further purification unless otherwise stated.

Chromatographic Methods

Column chromatography Column chromatographic separations were carried out at elevated pressure (flash chromatography) on silica gel 60 230-400 mesh from Merck KGaA (particle size: 0.040-0.063 mm). The eluent mixtures used and the ratios by volume v/v are indicated in the specifications below. The following abbreviations apply to the eluents used: DCM (dichloromethane), EE (ethyl acetate). H (n-hexane) and Tel (toluene).

Filtration: Filtrations for the removal of resulting solids were carried out using a G4 frit (pore width: 10-16 μm).

Analysis $^1$H-NMR spectroscopy:$^1$H-NMR spectra were recorded with a model AV 300 (300 MHz) and with the model Fourier 300 (300 MHz) from Bruker. Chemical shifts are stated in units on the δ-scale. The residual proton signals of the solvent (dichloromethane-$d_2$: δ=5.32 ppm, toluene-$d_8$:

δ=7.09; 7.00; 6.98: 2.09 ppm) served as standard.

$^{13}$C-NMR spectroscopy:$^{13}$C-NMR spectra were recorded with models AV 300 (75 MHz) and Fourier 300(75 MHz) from Bruker. The signal of the solvent (dichloromethane-$d_2$: δ=54.0 ppm, toluene-$d_8$:

δ=137.9; 129.2; 128.3; 125.5; 20.4 ppm) served as internal standard wherein the chemical shifts were taken from the broadband $^1$H-decoupled spectra.

$^{77}$Se-NMR spectroscopy:$^{77}$Se-NMR spectra were recorded with an AV 300 (57 MHz) from Bruker. The spectra were measured in broadband $^1$H-decoupled mode. The chemical shifts are reported in ppm.

Mass spectrometry: EI mass spectra were recorded on a Finnigan MAT 95 XP instrument from Thermo Electron and ESI-TOF mass spectra with a model 6210 Time-of-Flight LC/MS from Agilent.

Autoclave Experiments of Rhodium-Catalysed Hydroformylation

The hydroformylation was conducted in a 200 ml autoclave equipped with pressure-retaining valve, gas flow meter, sparging stirrer and pressure pipette from Prernex Reactor AG, Lengau, Switzerland. The toluene used as solvent was purified using a Pure Solv MD-7 System and stored under argon. The substrate 1-octene or n-octene used as substrate (EVONIK Industries AG, octene isomeric mixture of 1-octene: 3.3%; cis+trans-2-octene: 48.5%;

cis+trans-3-octene: 29.2%; cis+trans-octene-4: 16.4%; structurally isomeric octenes: 2.6%) was heated under reflux for several hours over sodium and distilled under argon.

For the experiments, solutions of the catalyst precursor and the ligand were mixed in the autoclave under an argon atmosphere. [(acac)Rh(COD)] (Umicore, acac=acetylacetonate anion; COD=1,5-cyclooctadiene) was used as catalyst precursor. For experiments at a concentration of 100 ppm-m rhodium, 10 mL of a 4.31 mM solution were placed in the autoclave. Subsequently, the mass of ligand corresponding to a ratio L/Rh=5:1 (or 1:1) was dissolved and mixed in 10 mL of toluene. By adding further toluene, the starting volume of the catalyst solution was adjusted to 41.0 mL Into a pressure-resistant pipette was filled: 1-octene or n-octene (10.70 g). The autoclave was heated to the temperatures stated in each case at a total gas pressure (synthesis gas: Linde; $H_2$(99.999%): CO (99.997%)=1:1) of a) 42 bar for a final pressure of 50 bar or b) 12 bar for a final pressure of 20 bar with stirring (1500 rpm). After reaching the reaction temperature, the synthesis gas pressure was increased to a) 48.5 bar for a final pressure of 50 bar or b) 19.5 bar for a final pressure of 20 bar and the reactant was introduced under a positive pressure of about 3 bar set in the pressure pipette. The reaction was conducted at a constant pressure of 50 or 20 bar (closed-loop pressure controller from Bronkhorst, the Netherlands) respectively over 4 h. After the reaction time had elapsed, the autoclave was cooled to room temperature, decompressed while stirring and purged with argon. 1.0 ml of each reaction mixture was removed immediately after the stirrer had been switched off, diluted with 5.0 ml of pentane and analysed by gas chromatography: HP 5890 Series II plus, PONA, 50m× 0.2mm×0.5 µm.

Abbreviations: calc.=calculated; RT=room temperature

The compound Ia (CAS 7304-91-8) is known from the literature. Ia was prepared according to: Canadian Journal of Chemistry, 88, 906-909, 2010.

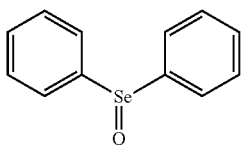

Ia

Diphenyl selenides may also be prepared according to the European patent application ER15168377.8. Diphenyl selenides may be prepared by this method by reacting at least one first arene and optionally a second arene at a defined temperature in the presence of selenium dioxide in acids, in particular in the presence of an acid having a pKa in the range of 0-5. A preferred temperature range is from 50 to 120° C. The reaction time, i.e. the conversion, takes place preferably over a period of days. The arenes may be substituted by hydrogen, alkyl and/or halogen.

Synthesis of diphenyl selenoxides I, in particular Ia. Analogously to the following synthetic procedure, the diphenyl selenoxides of the structure i may be prepared in accordance with the specified substituents.

175 µL (234 mg, 1.00 mmol, 1.0 eq) of diphenyl selenide were reacted with 140 mg (1.05 mmol, 1.05 eq) of N-chlorosuccinimide. After extractive work-up, 235 mg (0.940 mmol, 94%) of the title compound I were obtained as a colourless solid.

IR (ATR): (cm-1) =3044; 3008; 2989; 2941; 1570; 1470; 1437; 1300; 1156; 1069; 1056; 1047; 1017; 993; 915; 850; 820; 733; 686; 611; 481; 442, 1H-NMR (300 MHz, toluene-d8):

δ (ppm)=7.67-7.51 (m, 4H, Ar—CH); 7.16-6.87 (m, 6H, Ar—CH); 13C -NMR (75 MHz, toluene-d8): δ (ppm) =145.1; 130.5; 129.3; 126.0; 77Se-NMR (57 MHz, toluene-d8): δ (ppm)=851.0; HR-MS (ESI-TOF): calc. for C12H11O Se ([M+H]+): 250.99700, found: 250.99691;

calc. for C12H10OSeNa ([M+Na]+): 272.97894, found: 272.97888; C12H10OSe (249.99 g/mol). The analytical data are in agreement with the literature data.

Bis(3,5-dimethyl-2-hydroxypheny)selenium

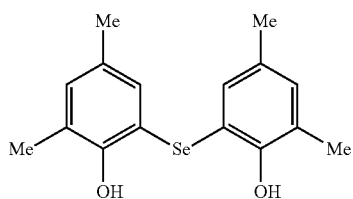

II

In a 250 mL round-bottom flask, 49.9 g of selenium dioxide (413 mmol) in 100 mL of pyridine were heated to 55° C. with the aid of an oil bath. 25 mL of 2,4-dimethylphenol (206 mmol) were then added and the temperature was maintained for seven and a half hours. On completion of the reaction, the mixture was diluted with 400 mL of ethyl acetate and filtered. The organic phase was washed with water and dried over magnesium sulphate, The pyridine was removed by distillation and the residue redissolved in ethyl acetate and washed with 10% hydrochloric acid and water in order to remove residues of pyridine. The organic phase was dried over magnesium sulphate and freed of the solvent under reduced pressure. The crude product thus obtained was heated under reflux in 400 mL of cyclohexane. After cooling to room temperature, the product crystallized. After one day, the product was filtered off, the filtrate was concentrated by half and again brought to crystallization at 4° C. This gave 18.56 g, 58 mmol (56%) of fine, pale yellow plates of the product $m_p$=120.1° C. (recrystallization from cyclohexane)

$^1$H NMR (400 MHz, CDCl$_3$) δ=7.11-7.12 (m, 2H), 6.90-6.92 (m, 2H), 5.95 (br, 2H, OH), 2.23 (s, 6H), 2.19 (s, 6H); $^{13}$C NMR (100 MHz, CDCl$_3$)δ=152.04, 133.35, 133.30, 130.67, 124.42, 115.31, 20.45, 16.69; $^{77}$Se NMR (76 MHz, CDCl$_3$) δ=164.91; HRMS for $C_{16}H_{18}O_2^{80}$ Se(ESI+)[M+ Na$^+$]: calculated: 345.0370; found: 445.0363;

elemental analysis for $C_{16}H_{18}O_2Se$: calculated: C: 59.82%, H: 5.65%; found: C: 59,69%, H: 5.76%.

Catalysis-hydroformylation

Scheme 1:
Presentation of the substances tested in the rhodium-catalysed hydroformylation.

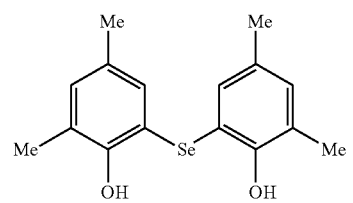

II

-continued

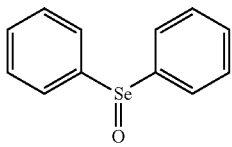

Ia

TABLE 1

Presentation of the catalysis experiments using organoselenium compounds

| Entry | Ligand | Olefin/ solvent | Rh/Ligand/ Olefin ratio | p [bar] | T [° C.] | t [h] | Y [%] | S [%] |
|---|---|---|---|---|---|---|---|---|
| 1 | II | n-octene/ toluene | 1:1:2197 (100 ppm Rh) | 50 | 120 | 4 | 9.5 | 33.2 |
| 3* | Ia | n-octene/ toluene | 1:1:2205 (40 ppm Rh) | 50 | 120 | 4 | 89.5 | 28.1 |

Notes on Table 1:
p = pressure,
T = temperature,
t = time,
Y = yield;
S = n-regioselectivity.
*= inventive examples The rhodium-catalysed hydroformyiation using compound II (entry 2) led to a yield of 9.5% (obtained from 90.5% resdiual olefin) and an n-regioselectivity of 33.2%.

The use of unprotected selenodiphenols II, i.e. those with two free OH groups, in the hydroformylation therefore leads to inhibition.

By using the diphenyl selenoxide Ia, a high yield of 89.5% in the hydroformylation with n-octene could be recorded.

Catalysis experiments 2) and 3) illustrate the successful use of diphenyl selenoxide in rhodium-catalysed hydroformylation. The object was therefore met.

The invention claimed is:
1. A method comprising the method steps of
   (i) initially charging at least one olefin,
   (ii) adding a complex comprising
      at least one diphenyl selenoxide of general structure (I)

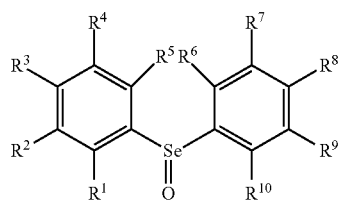

(I)

where $R^2$, $R^3$, $R^4$, $R^5$, $R^6$, $R^7$, $R^8$ and $R^9$ are each independently selected from the group consisting of —H, —$(C_1$-$C_{12})$-alkyl and -halogen, where alkyl is linear, branched or cyclic, the alkyl groups optionally being substituted by at least one —$(C_3$-$C_{12})$-cycloalkyl group, and where $R^1$ and $R^{10}$ are each independently —H, —$(C_1$-$C_{12})$-alkyl and/or halogen, where alkyl is linear, branched or cyclic, and at least one metal atom selected from the group consisting of Rh, Ru, Co and Ir or at least one diphenyl selenoxide of the general structure (I), as described above, and a substance having a metal atom selected from the group consisting of Rh, Ru, Co and Ir, (iii) feeding in $H_2$ and CO,
(iv) heating the reaction mixture,
wherein the olefin is converted to an aldehyde.

* * * * *